US006897332B2

(12) United States Patent
Belokon et al.

(10) Patent No.: US 6,897,332 B2
(45) Date of Patent: May 24, 2005

(54) PROCESS FOR THE CYANATION OF ALDEHYDES

(75) Inventors: Yuri Belokon, Moscow (RU); Michael North, London (GB)

(73) Assignees: Nesmeyanov Institute of Organoelement Compounds, Moscow (RU); King's College London, London (GB)

( * ) Notice: Subject to any disclaimer, the term of this patent is extended or adjusted under 35 U.S.C. 154(b) by 111 days.

(21) Appl. No.: 10/354,964

(22) Filed: Jan. 31, 2003

(65) Prior Publication Data

US 2003/0199706 A1 Oct. 23, 2003

Related U.S. Application Data

(63) Continuation-in-part of application No. PCT/GB01/03456, filed on Aug. 1, 2001, now abandoned.

(30) Foreign Application Priority Data

Aug. 2, 2000 (GB) .............................................. 0018973
May 24, 2002 (GB) .............................................. 0212017

(51) Int. Cl.$^7$ .......................................... C07C 253/00
(52) U.S. Cl. ...................... 558/308; 558/303; 558/311; 558/315; 502/232; 502/242; 502/247
(58) Field of Search ................................ 558/303, 308, 558/311, 315; 502/232, 242, 247

(56) References Cited

U.S. PATENT DOCUMENTS

| 4,336,206 A | | 6/1982 | Miindnich et al. ........ 260/465.4 |
| 5,508,458 A | * | 4/1996 | Zhao ........................... 556/45 |
| 5,756,803 A | * | 5/1998 | Casse et al. ................. 558/351 |
| 6,204,406 B1 | | 3/2001 | Mori et al. .................. 558/315 |
| 6,339,159 B1 | * | 1/2002 | Kobayashi et al. .......... 546/227 |

FOREIGN PATENT DOCUMENTS

| EP | 0 561 637 A2 | 9/1993 |
| JP | 6-271522 | 9/1994 |
| JP | 7-70040 | 3/1995 |

OTHER PUBLICATIONS

Chen et al, *J. Am. Chem. Soc.*, 122:9542–9543 (2000).
Tian et al, *J. Am. Chem. Soc.*, submitted Mar. 15, 2001.
Sumitomo Chemical Co., E 19. 1991–096042/14 (U.S. 6,204,406).
Hamashima et al, *J. Am. Chem. So.*, 122:7412–7413 (2000).
Hamashima et al, *Tetrahedron Letters*, 42:691–694 (2001).
Ichihara, *Tetrahedron Letters*, 42:695–697 (2001).
Belokon, Yuri N., et al, The Asymmetrical Addition of Trimethylsilyl Cyanide to Aldehydes Catalyzed by Chiral (Salen)Titanium Complexes, Journal of the American Chemical Society, vol. 121, 1999, pp. 3968–3973, XP002187021.

* cited by examiner

*Primary Examiner*—Golam M M Shameem
(74) *Attorney, Agent, or Firm*—Morgan, Lewis & Bockius LLP

(57) ABSTRACT

A process for cyanating an aldehyde is provided. The process comprises reacting the aldehyde with:
i) a cyanide source which does not comprise a Si—CN bond or a C—(C=O)—CN moiety; and
ii) a substrate susceptible to nucleophilic attack not comprising a halogen leaving group;
in the presence of a chiral catalyst. Preferably, the chiral catalyst is a chiral vanadium or titanium catalyst. The cyanide source is preferably an alkali metal cyanide and the substrate susceptible to nucleophilic attack not comprising a halogen leaving group is a carboxylic anhydride.

15 Claims, No Drawings

PROCESS FOR THE CYANATION OF ALDEHYDES

This is a continuation-in-part of application PCT/GB01/03456 filed Aug. 1, 2001, now abandoned, which is hereby incorporated by reference in its entirety.

This invention relates to a process for the cyanation of aldehydes, particularly to the asymmetric cyanation of aldehydes, including the synthesis of chiral cyanohydrins and derivatives thereof, such as chiral O-acyl cyanohydrins.

The synthesis of chiral intermediates such as chiral cyanohydrins and derivatives is an important process for use in the manufacture of fine chemicals, agrochemicals and pharmaceuticals. Enantiomerically pure cyanohydrins and derivatives are known to be versatile intermediates for the synthesis of a wide range of commercially important compounds. For example chiral cyanohydrins and derivatives are intermediates for the synthesis of: α-hydroxy-acids, α-amino alcohols, and 1,2-diols. In addition, chiral cyanohydrins are themselves components of highly successful pyrethroid insecticides.

There are a number of synthetic routes available for the asymmetric synthesis of cyanohydrins and derivatives, virtually all of which involve the use of a chiral catalyst to induce the asymmetric addition of a cyanide source to a prochiral aldehyde or ketone. The available catalysts include enzymes, cyclic peptides and transition metal complexes. However, all of these methods suffer from one or more significant disadvantages which have negated their commercial exploitation. Many of the methods employ highly toxic and hazardous HCN, require very low (ca. −80° C.) reaction temperatures, and/or give products with low to moderate enantiomeric excesses.

Processes for the asymmetric synthesis cyanohydrins and derivatives are disclosed by M. North, Synlett, 1993, 807–20; F. Effenberger, Angew. Chem. Int. Ed. Engl. 1994, 33, 1555; M. North, Comprehensive Organic Functional Group Transformations ed. Katritzky, A. R.; Meth-Cohn, O.; Rees, C. W.; Pattenden, G.; Pergamon Press, Oxford, 1995, vol. 3, chapter 18; Y. Belokon' et al, Tetrahedron Asymmetry, 1996, 7, 851–5; Y. Belokon' et al, J. Chem. Soc., Perkin Trans. 1, 1997, 1293–5; Y. N. Belokon' et al, Izvestiya Akademii Nauk. Seriya Khimicheskaya, 1997, 2040: translated as Russian Chem. Bull., 1997, 46, 1936–8; V. I. Tararov et al, Chem. Commun., 1998, 387–8; Y. N. Belokon' et al, J. Am. Chem. Soc., 1999, 121, 3968–73; V. I. Tararov et al, Russ. Chem. Bull., 1999, 48, 1128–30; Y. N. Belokon' et al, Tetrahedron Lett., 1999, 40, 8147–50; Y. N. Belokon' et al, Eur. J. Org. Chem., 2000, 2655–61; Y. N. Belokon', M. North, and T. Parsons; Org. Lett., 2000, 2, 1617–9.

In particular J. Am. Chem. Soc., 1999, 121, 3968–73 discloses the use of catalysts 1 and 2 having the formulae given below (with $R^1$ and $R^2$=tert-butyl) which are the most active catalysts known for this reaction (Scheme 1).

Scheme 1

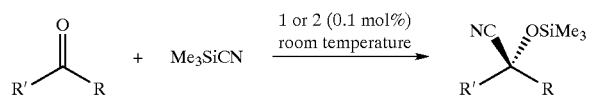

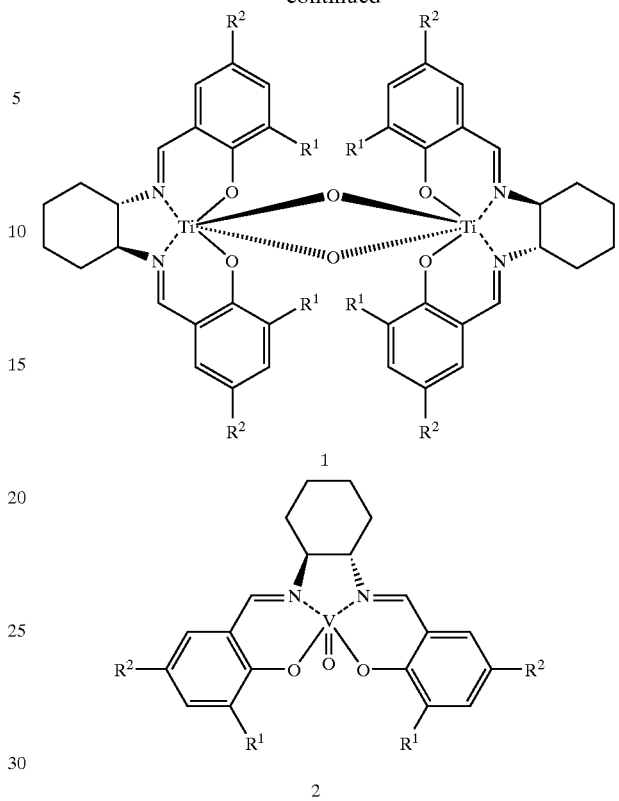

wherein each $R^1$ and $R^2$ independently is H, alkyl, aryl, aralkyl, alkoxy, aryloxy, halogen, nitro, halo-alkyl, amino (including with alkyl or aryl substituents on the nitrogen atom), or amido. Preferably, $R^1$ and $R^2$=CMe$_3$. However, whilst the chemistry shown in Scheme 1 is academically interesting, it is of little commercial relevance due to the prohibitive cost of trimethylsilyl cyanide. Additionally, trimethylsilyl cyanide is highly volatile and hazardous to handle.

According to a first aspect of the present invention, there is provided a process for cyanating an aldehyde which comprises reacting the aldehyde with:
i) a cyanide source which does not comprise a Si—CN bond or a C—(C=O)—CN moiety; and
ii) a substrate susceptible to nucleophilic attack not comprising a halogen leaving group;
in the presence of a chiral catalyst.

Aldehydes which can be employed in the process of the present invention have the chemical formula R—CHO, wherein R is a substituted or unsubstituted hydrocarbyl group, including perhalogenated hydrocarbyl groups. Hydrocarbyl groups which may be represented by R include alkyl, alkenyl, aryl and heterocyclic groups, and any combination thereof, such as aralkyl and alkaryl, for example benzyl groups.

Alkyl groups which may be represented by R include linear and branched alkyl groups comprising up to 20 carbon atoms, particularly from 1 to 7 carbon atoms and preferably from 1 to 5 carbon atoms. When the alkyl groups are branched, the groups often comprise up to 10 branched chain carbon atoms, preferably up to 4 branched chain atoms. In certain embodiments, the alkyl group may be cyclic, commonly comprising from 3 to 10 carbon atoms in the largest ring and optionally featuring one or more bridging rings. Examples of alkyl groups which may be represented by R include methyl, ethyl, propyl, 2-propyl, butyl, 2-butyl, t-butyl and cyclohexyl groups.

Alkenyl groups which may be represented by R include $C_{2-20}$, and preferably $C_{2-6}$ alkenyl groups. One or more carbon-carbon double bonds may be present. The alkenyl group may carry one or more substituents, particularly phenyl substituents. Examples of alkenyl groups include vinyl, styryl and indenyl groups.

Aryl groups which may be represented by R may contain 1 ring or 2 or more fused rings which may include cycloalkyl, aryl or heterocyclic rings. Examples of aryl groups which may be represented by R include phenyl, tolyl, fluorophenyl, chlorophenyl, bromophenyl, trifluoromethylphenyl, anisyl, naphthyl and ferrocenyl groups.

Perhalogenated hydrocarbyl groups which may be represented by R include perhalogenated alkyl and aryl groups, and any combination thereof, such as aralkyl and alkaryl groups. Examples of perhalogenated alkyl groups which may be represented by R include —$CF_3$ and —$C_2F_5$.

Heterocyclic groups which may be represented by R include aromatic, saturated and partially unsaturated ring systems and may constitute 1 ring or 2 or more fused rings which may include cycloalkyl, aryl or heterocyclic rings. The heterocyclic group will contain at least one heterocyclic ring, commonly comprisING from 3 to 7 ring atoms in which at least one atom is carbon and at least one atom is any of N, O, S or P. Examples of heterocyclic groups which may be represented by R include pyridyl, pyrimidyl, pyrrolyl, thiophenyl, furanyl, indolyl, quinolyl, isoquinolyl, imidazoyl and triazoyl groups.

When R is a substituted hydrocarbyl or heterocyclic group, the substituent(s) should be such so as not to adversely affect the reaction. Optional substituents include halogen, cyano, nitro, hydroxy, amino, thiol, acyl, hydrocarbyl, perhalogenated hydrocarbyl, heterocyclyl, hydrocarbyloxy, mono or di-hydrocarbylamino, hydrocarbylthio, esters, carbonates, amides, sulphonyl and sulphonamido groups wherein the hydrocarbyl groups are as defined for R above. One or more substituents may be present.

Cyanide sources not comprising a Si—CN bond or a C—(C=O)—CN moiety which can be employed in the process of the present invention include dicyanogen; ammonium cyanide salts, particularly quaternary ammonium salts such as tetraalkyl, preferably tetra $C_{1-6}$alkyl-, ammonium salts; sulfonyl cyanides, for example tosyl cyanide and mesyl cyanide; and organic cyanides having the formula $R^3$—O—CO—CN, where $R^3$ is H or a substituted or unsubstituted hydrocarbyl group as described above, commonly a $C_{1-6}$ alkyl group. In many embodiments, the cyanide source is an inorganic cyanide, preferably a metal cyanide or an in situ source of inorganic cyanide such as acetone cyanohydrin. Particularly preferred cyanide sources comprise alkali metal and alkaline earth metal cyanides, for example, lithium, sodium, potassium, rubidium, caesium, magnesium and calcium cyanides. The most preferred cyanide source is potassium cyanide.

The reaction between the aldehyde and the cyanide source occurs in the presence of a substrate susceptible to nucleophilic attack which does not comprise a halogen leaving group. Examples of such substrates are compounds having the general formula Q-Y, wherein Q represents an organic acid radical, and Y represents a non-halogen leaving group. In many embodiments, the leaving group, Y, is a leaving group the conjugate acid of which has a pKa of greater than about −2, such as greater than 3, and often less than 12.

Examples of leaving groups include alkyl and aryl sulphonates, such as mesylate and tosylate; carbonates; especially alkyl carbonates; carboxylates, especially alkyl carboxylates; and groups of formula —$NR^xR^y$, wherein $R^x$ and $R^y$ together with the nitrogen atom form an unsaturated heterocyclic ring which may comprise one or more additional heteroatoms, especially nitrogen, particularly imidazole or benzimidazole rings. Organic acid radicals which may be represented by Q include groups of formulae R—(C=O)—, R—(C=S)—, RO—(C=O)—, RN—(C=O)—, RO—(C=S)—, RN—(C=S)—, RS—(C=O)—, RS—(C=S)—, R—(P=O)(OR)—, R—$SO_2$— and R—SO—, wherein R represents a substituted or unsubstituted hydrocarbyl group as described above.

In many embodiments, the substrate susceptible to nucleophilic attack which does not comprise a halogen leaving group has the general formula $R^4$—(C=X)-A-Z, wherein $R^4$ represents an organic radical, such as a substituted or unsubstituted hydrocarbyl group as described above or a hydrocarbyloxy group wherein the hydrocarbyl moiety is as described above; X represents O, S, N—R or NOR wherein R represents H or a substituted or unsubstituted hydrocarbyl group as described above; A represents a chalcogen, preferably O or S and Z represents a group of formula (C=O)—$R^4$ or (C=S)—$R^4$ wherein $R^4$ is as described above; or -A-Z represents a group of formula —$NR^xR^y$ as described above. Preferably, X and A each represent O, and Z is a group of formula (C=O)—$R^4$.

Commonly, the substrate susceptible to nucleophilic attack which does not comprise a halogen leaving group is a carboxylic acid anhydride or an anhydride of a carbonic acid. Carboxylic anhydrides include mixed anhydrides and are often the anhydrides of $C_{1-8}$ alkyl or aryl carboxylic acids, such as acetic anhydride and trifluoroacetic anhydride. Carbonic acid anhydrides include di-tert-butyldicarbonate, (tBuOCOOCOOtBu), N,N'-disuccinyldicarbonate, N,N'-dimaleimyldicarbonate, N-(tert-butyl-oxycarbonyloxy) maleimide or succinimide, and N-(benzyloxycarbonyloxy) maleimide or succinimide.

Chiral catalysts that can be employed in the process of the present invention are those known in the art for catalysing the addition of a cyanide group to a carbonyl group, and include enzymes and cyclic peptides. Preferably, the chiral catalysts are metal complexes of metals, for example B, Mg, Al, Sn, Bi, particularly transition-metal complexes comprising a chiral ligand, for example Re and lanthanides. In many embodiments, the transition metal is a Lewis acid capable of forming tetra coordinate complexes with chiral ligands. Preferred transition metal complexes are complexes of titanium and vanadium, especially titanium (IV) and vanadium (V). The chiral ligands are preferably tetradentate and commonly coordinate via oxygen and/or nitrogen atoms. Examples include binol, taddol, sulfoximines, salicylimines and tartrates, especially tartrate esters. However, the most preferred class of ligands are chiral Salen ligands and derivatives thereof. Particularly preferably, the chiral catalyst employed in the process according to the present invention is a catalyst of formula 1 or 2 described above. When a catalyst of formula 1 is employed, it is also possible to use a mixed catalyst containing one vanadium and one titanium ion in each bimetallic catalyst unit.

The process according to the present invention is commonly carried out in the presence of a solvent. Preferred solvents are polar, aprotic solvents, including halocarbons, for example dichloromethane, chloroform and 1,2-dichloroethane; nitriles, for example acetonitrile; ketones, for example acetone and methylethylketone; ethers, for example diethylether and tetrahydrofuran; and amides, for example dimethylformamide, dimethylacetamide and N-methylpyrolidinone.

Advantageously, the process of the present invention is carried out in the presence of an additive which accelerates the rate of reaction. Commonly these additives are inorganic bases such as $Na_2CO_3$, $K_2CO_3$ or $CaCO_3$ or comprise a nucleophilic heteroatom, and often have pKa of greater than 10, for example in the range from 15–35, such as from 15–25. Examples of preferred additives include organic bases, such as pyridine, 2,6-lutidine and imidazole; alcohols, such as $C_{1-6}$ alcohols, especially tertiary alcohols such as t-butanol; and water.

It will be recognised that when the cyanide source is a metal cyanide, the reaction mixture will be heterogeneous. In such circumstances, it is therefore desirable to employ efficient agitation of the reaction mixture. Agitation means known in the art, for example mechanical stirrers and ultrasonic agitators, selected appropriately according to the scale of reaction can be employed as desired.

The process of the present invention is often carried out a temperature of from about $-40°$ C. to about $40°$ C. Lower temperatures may be employed if desired, although they are not believed to be advantageous. Commonly, the reaction is carried out a temperature of from $-25°$ C. to ambient temperature, such as $15–25°$ C.

The product of the cyanation reaction in the presence of the substrate susceptible to nucleophilic attack which does not comprise a halogen leaving group can then be reacted, for example by hydrolysis, to form a cyanohydrin. When the substrate susceptible to nucleophilic attack which does not comprise a halogen leaving group has the general formula Q-Y, the process can be represented by the sequence:

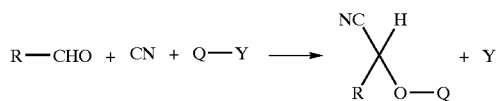

The process according to the present invention is particularly suited to the enantioslective cyanation of aldehydes. It has been found that particularly effective enantioselective cyanation of aldehydes can be achieved by employing an order of addition in which a mixture of chiral catalyst, cyanide source, solvent and aldehyde are prepared, and preferably an additive as described above is added to this mixture. The temperature of this mixture is then adjusted to the desired reaction temperature if necessary, and the substrate susceptible to nucleophilic attack not comprising a halogen leaving group is added. This approach has been found to be especially suited when the additive comprises lutidine and the substrate susceptible to nucleophilic attack not comprising a halogen leaving group is a carboxylic anhydride.

Certain embodiments of the present invention comprise the use of a heterogeneous mixture of an alkali metal cyanide, or alkaline earth metal cyanide (or other inexpensive cyanide sources such as acetone cyanohydrin), an additive (which may be a base e.g. pyridine; or water) and acetic anhydride (or other carboxylic acid anhydrides) to generate a cyanating agent for aldehydes. This can be carried out in situ with catalyst 1 (and related catalysts) and an aldehyde to generate chiral O-acyl cyanohydrins (conditions as illustrated in Scheme 2). This methodology uses only inexpensive reagents, and produces cyanohydrin derivatives which are not sensitive to moisture and do not spontaneously racemize.

Scheme 2

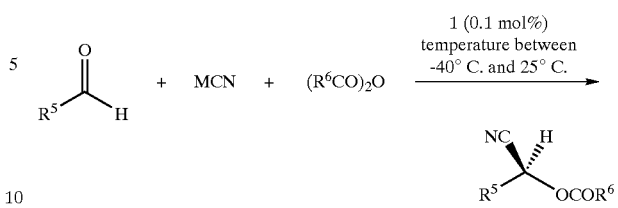

$R^5$=alkyl, aryl, aralkyl, and may contain halogen, oxygen, nitrogen, or sulfur atoms within the group. $R^6$=alkyl, aryl, aralkyl, and may contain halogen, oxygen, nitrogen, or sulfur atoms within the group. M=alkali metal or alkaline earth metal. Preferably, potassium cyanide is used as the cyanide source, acetic anhydride as the anhydride, 2,6-lutidine as the additive and catalyst 1 (or the corresponding enantiomer derived from (R,R-cyclohexane-1,2-diamine) with $R^1$ and $R^2={}^tBu$ is used as the catalyst.

This invention allows the synthesis of chiral cyanohydrin derivatives derived from a wide variety of aldehydes. The products can be transformed into other chiral compounds by standard chemistry using either of the acyl or nitrile functional groups.

According to one preferred aspect of the present invention there is provided a process for the cyanation of an aldehyde group which comprises reacting the aldehyde with:
i) an alkali metal cyanide; and
ii) a carboxylic anhydride;
in the presence of a catalyst comprising a chiral complex of titanium or vanadium.

According to another preferred aspect of the present invention there is provided a process for the preparation of an O-acyl cyanohydrin which comprises reacting an aldehyde with potassium cyanide and a carboxylic anhydride in the presence of a catalyst comprising a chiral complex of titanium or vanadium.

In the preferred aspects, further preferences are as described above with respect to the first aspect of the present invention.

In certain embodiments, the chiral transition metal catalyst and a metal cyanide can be added as mixture. Such a mixture is believed to be a novel composition of matter, and accordingly forms another aspect of the present invention. Preferred transition metal catalysts and metal cyanides are as described above with respect to the first aspect of the present invention.

There is also a need for new catalysts for use in asymmetric cyanation of aldehydes.

According to a further aspect of the present invention, there is provided a catalyst of formula (3a) or (3b):

(3a)

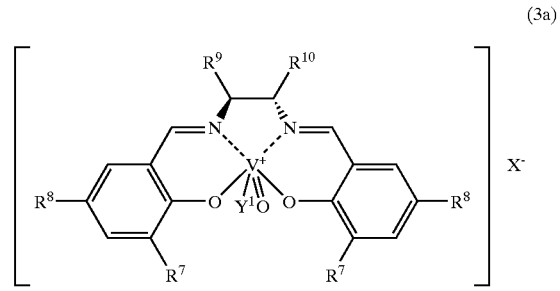

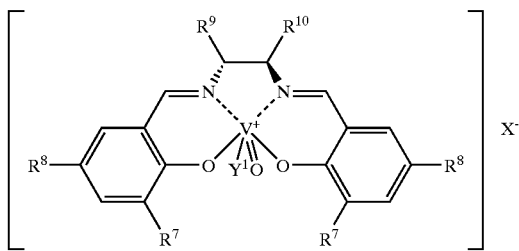

(3b)

wherein,

R⁷ and R⁸ are independently hydrogen, halogen, cyano, nitro, hydroxy, amino, thiol, an optionally substituted hydrocarbyl, perhalogenated hydrocarbyl, an optionally substituted heterocyclyl, an optionally substituted hydrocarbyloxy, an optionally substituted mono or di-hydrocarbylamino, an optionally substituted hydrocarbylthio, an optionally substituted acyl, an optionally substituted ester, an optionally substituted carbonate, an optionally substituted amide, or an optionally substituted sulphonyl or sulphonamido group, or comprise part of a fused ring;

R⁹ and R¹⁰ are independently halogen, cyano, nitro, hydroxy, amino, thiol, an optionally substituted hydrocarbyl, perhalogenated hydrocarbyl, an optionally substituted heterocyclyl, an optionally substituted hydrocarbyloxy, an optionally substituted mono or di-hydrocarbylamino, an optionally substituted hydrocarbylthio, an optionally substituted acyl, an optionally substituted ester, an optionally substituted carbonate, an optionally substituted amide, or an optionally substituted sulphonyl or sulphonamido group, or R⁹ & R¹⁰ optionally are linked in such a way as to form an optionally substituted ring(s);

Y¹ is a neutral ligand; and

X is an anion.

Hydrocarbyl groups which may be represented by R⁷⁻¹⁰ independently include alkyl, alkenyl and aryl groups, and any combination thereof, such as aralkyl and alkaryl, for example benzyl groups Alkyl groups which may be represented by R⁷⁻¹⁰ include linear and branched alkyl groups comprising up to 20 carbon atoms, particularly from 1 to 7 carbon atoms and preferably from 1 to 5 carbon atoms. When the alkyl groups are branched, the groups often comprise up to 10 branched chain carbon atoms, preferably up to 4 branched chain atoms. In certain embodiments, the alkyl group may be cyclic, commonly comprising from 3 to 10 carbon atoms in the largest ring and optionally featuring one or more bridging rings. Examples of alkyl groups which may be represented by R⁷⁻¹⁰ include methyl, ethyl, propyl, 2-propyl, butyl, 2-butyl, t-butyl, t-pentyl, cyclohexyl and adamantyl groups.

Alkenyl groups which may be represented by R⁷⁻¹⁰ include C₂₋₂₀, and preferably C₂₋₆ alkenyl groups. One or more carbon-carbon double bonds may be present. The alkenyl group may carry one or more substituents, particularly phenyl substituents. Examples of alkenyl groups which may be represented by R⁷⁻¹⁰ include vinyl, styryl and indenyl groups.

Aryl groups which may be represented by R⁷⁻¹⁰ may contain 1 ring or 2 or more fused rings which may include cycloalkyl, aryl or heterocyclic rings. Examples of aryl groups which may be represented by R⁷⁻¹⁰ include phenyl, tolyl, fluorophenyl, chlorophenyl, bromophenyl, trifluoromethylphenyl, anisyl, naphthyl and ferrocenyl groups.

Perhalogenated hydrocarbyl groups which may be represented by R⁷⁻¹⁰ include perhalogenated alkyl and aryl groups, and any combination thereof, such as aralkyl and alkaryl groups. Examples of perhalogenated alkyl groups which may be represented by R⁷⁻¹⁰ include —CF₃ and —C₂F₅.

Heterocyclic groups which may be represented by R⁷⁻¹⁰ include aromatic, saturated and partially unsaturated ring systems and may constitute 1 ring or 2 or more fused rings which may include cycloalkyl, aryl or heterocyclic rings. The heterocyclic group will contain at least one heterocyclic ring, commonly comprising from 3 to 7 ring atoms in which at least one atom is carbon and at least one atom is any of N, O, S or P. Examples of heterocyclic groups which may be represented by R⁷⁻¹⁰ include pyridyl, pyrimidyl, pyrrolyl, thienyl, furanyl, indolyl, quinolyl, isoquinolyl, imidazoyl and triazoyl groups.

When R⁹ & R¹⁰ are linked in such a way as to form an optionally substituted ring(s), commonly comprising from 5 to 7 ring atoms.

When R⁷⁻¹⁰ is a substituted hydrocarbyl, heterocyclic group, hydrocarbyloxy, mono or di-hydrocarbylamino, hydrocarbylthio, acyl, ester, carbonate, amide, sulphonyl or sulphonamido group, or R⁹ & R¹⁰ are linked in such a way as to form a substituted ring(s) the substituent(s) should be such so as not to adversely affect the reaction. Optional substituents include halogen, cyano, nitro, hydroxy, amino, thiol, acyl, hydrocarbyl, perhalogenated hydrocarbyl, heterocyclyl, hydrocarbyloxy, mono or di-hydrocarbylamino, hydrocarbylthio, esters, carbonates, amides, sulphonyl and sulphonamido groups wherein the hydrocarbyl groups are as defined above for R⁷⁻¹⁰. One or more substituents may be present.

Neutral ligands which may be represented by Y¹ include water, C₁₋₄ alcohols, C₁₋₄ thiols, C₁₋₈ ethers, C₁₋₈ thioethers, C₁₋₈ primary, secondary or tertiary amines, and aromatic amines for example pyridine. A preferred ligand represented by Y¹ is water.

Anions which may be represented by X include, halide, sulphate, alkylsulphate, perchlorate, PF₆⁻, acetate, tosylate and triflate.

Preferably, R⁷ or R⁸ are independently alkyl groups, preferably methyl, ethyl, propyl, 2-propyl, butyl, 2-butyl, t-butyl, t-pentyl and cyclohexyl groups.

More preferably R⁷ and R⁸ are independently 2-propyl, butyl, 2-butyl, t-butyl, t-pentyl and cyclohexyl groups.

Most preferably R⁷ and R⁸ are independently t-butyl, t-pentyl and cyclohexyl groups.

Preferably R⁹ and R¹⁰ are independently halogen, cyano, nitro, an optionally substituted hydrocarbyl, perhalogenated hydrocarbyl, an optionally substituted heterocyclyl, an optionally substituted hydrocarbyloxy, an optionally substituted di-hydrocarbylamino, an optionally substituted hydrocarbylthio, an optionally substituted acyl, an optionally substituted ester, an optionally substituted carbonate, an optionally substituted amide, or an optionally substituted sulphonyl or sulphonamido group, or R⁹ & R¹⁰ optionally being linked in such a way as to form an optionally substituted ring(s)

More preferably R⁹ and R¹⁰ are independently alkyl or aryl groups, or R⁹ & R¹⁰ are linked in such a way as to form an optionally substituted ring comprising from 5 to 7 ring atoms, the ring atoms preferably are carbon atoms.

More preferably when R⁹ and R¹⁰ are independently alkyl or aryl groups, the alkyl or aryl groups are methyl or phenyl groups.

More preferably when R⁹ & R¹⁰ are linked in such a way as to form an optionally substituted ring, the ring comprises 6 ring atoms and the ring atoms are preferably carbon atoms.

Most preferably $R^9$ & $R^{10}$ are linked in such a way as to form an un-substituted ring comprising 6 ring atoms and the ring atoms are carbon atoms.

Preferred catalysts are those in which $R^7$ and $R^8$ are independently 2-butyl, t-butyl, t-pentyl or cyclohexyl groups, and $R^9$ and $R^{10}$ are independently methyl or phenyl groups, or $R^9$ & $R^{10}$ are linked in such a way as to form an optionally substituted ring comprising 6 ring atoms, the ring atoms being carbon atoms.

More preferred catalysts are those in which $R^7$ and $R^8$ are independently 2-butyl, t-butyl, t-pentyl or cyclohexyl groups, and $R^9$ and $R^{10}$ are independently methyl or phenyl groups, or $R^9$ & $R^{10}$ are linked in such a way as to form an optionally substituted ring comprising 6 ring atoms, the ring atoms being carbon atoms Most preferred catalysts are those in which $R^7$ and $R^8$ are independently 2-butyl, t-butyl, or t-pentyl groups, and $R^9$ & $R^{10}$ are linked in such a way as to form an optionally substituted ring comprising 6 ring atoms, the ring atoms being carbon atoms.

Catalysts according to the present invention may be prepared by reaction of a suitable compound of vanadium with a ligand in the presence of oxygen.

Typically vanadyl sulphate hydrate is reacted with a Salen ligand in solvent in the presence of oxygen.

Catalysts according to the present invention have been found to be useful in the processes for the cyanation of aldehydes which are described above.

According to a further preferred aspect of the present invention there is provided a process for cyanating an aldehyde which comprises reacting the aldehyde with:
i) a cyanide source which does not comprise a Si—CN bond or a C—(C=O)—CN moiety; and
ii) a substrate susceptible to nucleophilic attack not comprising a halogen leaving group;
in the presence of a chiral catalyst of formula (3a) or (3b).

The chiral catalyst of formula (3a) or (3b) is as described above in connection with the previous aspect of the present invention.

Aldehydes, cyanide sources, substrates and process conditions which can be employed in the process of the present invention are as described above in connection with the first aspect of the present invention.

Advantageously, the use of the catalysts of the present invention in these processes may facilitate the reactions being carried out at temperatures which are higher than those which can be employed with other catalysts (particularly Ti(IV) catalysts) and still exhibit a high degree of enantio-selectivity.

According to one preferred aspect of the present invention there is provided a process for the cyanation of an aldehyde group which comprises reacting the aldehyde with:
i) an alkali metal cyanide; and
ii) a carboxylic anhydride;
in the presence of a catalyst of formula (3a) or (3b).

The chiral catalyst of formula (3a) or (3b) is as described above in connection with the first aspect of the present invention.

Aldehydes, metal cyanides, carboxylic anhydrides and process conditions which can be employed in the process of the present invention are as described above in connection with the further aspects of the first aspect of the present invention According to another preferred aspect of the present invention there is provided a process for the preparation of an O-acyl cyanohydrin which comprises reacting an aldehyde with potassium cyanide and a carboxylic anhydride in the presence of a catalyst of formula (3a) or (3b).

The chiral catalyst of formula (3a) or (3b) is as described above in connection with the first aspect of the present invention.

In the preferred aspects, further preferences are as described above with respect to the first aspect of the present invention.

In certain embodiments, the chiral transition metal catalyst of formula (3a) or (3b) and a metal cyanide can be added as mixture. Such a mixture is believed to be a novel composition of matter, and accordingly forms another aspect of the present invention. Preferred transition metal catalysts and metal cyanides are as described above with respect to the first aspect of the present invention.

The invention is illustrated, without limitation, by the following examples. In the examples, catalyst 1a has the formula:

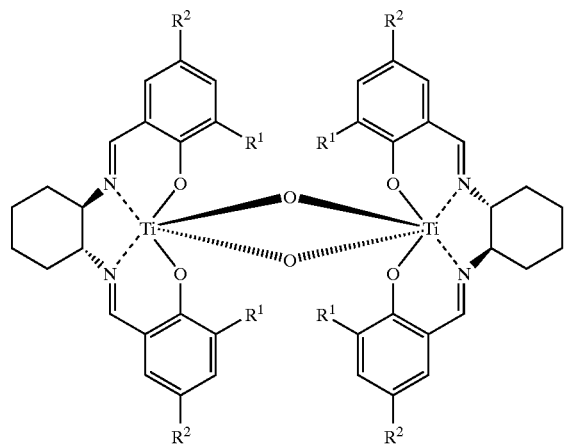

and catalyst 1b has the formula:

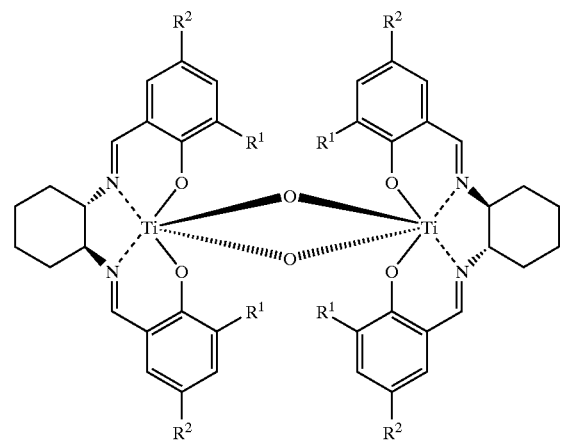

General Methods $^1$H NMR spectra were recorded at 250 MHz on a Bruker AM250 spectrometer, and at 400 MHz on a Bruker AMX-400 spectrometer (at 293 K, CDCl$_3$ or CD$_2$Cl$_2$). Spectra were internally referenced either to TMS or to the residual solvent peak, and peaks are reported in ppm downfield of TMS.

Infrared spectra of solutions were measured with a Nicolet Magna-750 Fourier-transform spectrometer with a resolution of 2 cm$^{-1}$. The spectra were recorded using a 0.06 mm KBr cell. Solvent spectra were subtracted from solution spectra using the OMNIC Nicolet program.

Optical rotations were recorded on an Optical Activity Ltd. Polar 2001 or a Perkin-Elmer 241 polarimeter, and are reported along with the solvent and concentration in g/100 mL. Elemental analyses were performed on a Carlo Erba Model 1106 or Model 1108 analyser. Chiral GC was carried out on a DP-TFA-γ-CD, fused silica capillary column (32 m×0.2 mm) using helium as the carrier gas.

Dichloromethane was distilled over $CaH_2$.

Acetic anhydride was distilled from the commercial product (99%).

Commercial potassium cyanide (98%) was thoroughly powdered and stored in vacuo over $P_2O_5$.

Aliphatic and aromatic aldehydes were purified by usual methods.

Chiral ligands were prepared by refluxing 1,2-cyclohexyldiamines (R,R and S,S) with 2,4-di-tert-butyl salicylaldehyde.

EXAMPLE 1

To a mixture of KCN (5.0 g, 77 mmol) and catalyst 1a ($R^1=R^2={}^tBu$)(0.3 g, 0.25 mmol) in $CH_2Cl_2$ (60 ml) were added with stirring benzaldehyde (2.5 ml, 25 mmol), 2,6-lutidine (0.28 ml, 2.4 mmol) and water (0.4 ml, 24 mmol). The reaction mixture was cooled to −30° C. and $Ac_2O$ (5 ml, 53 mmol) was added. The reaction mixture was stirred for 10 hours at −30° C. and then filtered, passed through a $SiO_2$ column (1 cm×10 cm) in a mixture of hexane/AcOEt 10:1 to remove the catalyst. The filtrate was evaporated and distilled in vacuo to give 2.7 g (63%) of O-Acetyl (S)-mandelonitrile with 87% enantiomeric excess as determined by chiral gas chromatography.

The experimental procedure was employed with a range of aldehydes under the same conditions, except the reaction temperature. The temperature employed and the results achieved are given in Table 1 below.

TABLE 1

| $R^1$ (R = H) | Temperature = 24° C. ee (%) | Temperature = −40° C. Ee (%) | Temperature = −78° C. ee (%) |
|---|---|---|---|
| $C_6H_5$ | 80 | 90 | 86 |
| 4-$CF_3C_6H_4$ | 60 | 76 | 54 |
| 4-$FC_6H_4$ | 65 | 90 | 84 |
| 4-$ClC_6H_4$ | — | 90 | — |
| 2-$FC_6H_4$ | 45 | 86 | 88 |
| 3-$PhOC_6H_4$ | — | 90 | — |
| $C_6H_5CH_2CH_2$ | 40 | 82 | — |
| $(CH_3)_2CH$ | — | 64 | — |
| $(CH_3)_3C$ | 40 | 62 | — |

The reactions can be run at room temperature, giving quantitative chemical yields in 2–3 hours or at lower temperatures, the latter giving better enantiomeric excesses, though at the expense of lower chemical yields (40–70%) and longer reaction times (10 hours).

EXAMPLE 2

The method of Example 1 was repeated for the cyanation of 3-phenyl propanal at −35° C., except that imidazole was employed in place of 2,6-lutidine. The O-acetyl cyanohydrin was obtained in 90% yield and 85% ee.

EXAMPLE 3

The method of Example 1 was repeated, except that catalyst 1a wherein $R^1$=Ph, and $R^2$=H gave a 90% chemical yield and 82% ee when used at −35° C. with benzaldehyde as substrate.

EXAMPLE 4

A stirred mixture of KCN (12.37 g, 0.19 mol), catalyst 1b (0.487 g, 4×10⁻⁴ mol), t-BuOH (3.7 g, 4.8 mL, 5.0×10⁻² mol) and 2-chlorobenzaldehyde (6.68 g, 5.35 mL, 4.75×10⁻² mol) in dry dichloromethane (120 mL) was cooled to −42° C., and acetic anhydride (19.4 g, 17.9 mL, 0.19 mol) was then added in one portion. The reaction mixture was stirred for 7 hours at the same temperature. Solid salts were filtered and washed thoroughly with dichloromethane. To remove the catalyst the filtrate was passed through a pad of silica (10 mm×50 mm) eluting with dichloromethane. The solvent was evaporated, and the resulting yellowish residue distilled in vacuo affording (R)-2-chlorobenzaldehyde cyanohydrin acetate. Yield 8.87 g (88.6%); b.p. 127–130° C. (0.2 mm); ee (R), 88.3%; $[\alpha]_D^{25}$ =+27.4° (c=1, in $CHCl_3$); $n_D^{25}$=1.5189; $^1H$ NMR (200 MHz, $CDCl_3$, 25° C.): δ=2.15 (s, 3H; $CH_3$); 6.66 (s, 1H; CH); 7.32–7.70 (m, 4H; ArH). Elemental analysis (%) calculated for $C_{10}H_8ClNO_2$: C, 57.30, H, 3.85, Cl, 16.91, N, 6.68; found C, 56.93, H, 3.83, Cl, 17.03, N, 6.69.

The procedure was repeated using different aldehydes and catalysts. Details of the aldehydes and catalysts employed, and the results obtained, are given in Table 2 below. Chemical yields were measured by NMR, unless specified otherwise.

TABLE 2

Enantioselective synthesis of O-acetyl cyanohydrins, according to Scheme 2 promoted by 1a or 1b.[a]

| Aldehyde | Catalyst | Chemical Yield, % | Enantiomeric Excess, ee %[c] Configuration |
|---|---|---|---|
| PhCHO | 1a [1b] | 93 [92[b]] | 90(S) [89(R)] |
| p-$MeOC_6H_4CHO$ | 1b | 74 | 93(R) |
| m-$MeOC_6H_4CHO$ | 1b | [99] | 93(R) |
| m-$PhOC_6H_4CHO$ | 1a [1b] | 99 [99] | 90(S) [89(R)] |
| p-$FC_6H_4CHO$ | 1a [1b] | 98 [99] | 92(S) [93(R)] |
| o-$FC_6H_4CHO$ | 1a [1b] | 87 [86] | 85(S) [82(R)] |
| m-$FC_6H_4CHO$ | 1b | 99 | 89(R) |
| o-$ClC_6H_4CHO$ | 1a [1b] | 87 [89[d]] | 86(S) [88(R)] |
| $PhCH_2CH_2CHO$ | 1a [1b] | 80 [79[d]] | 84(S) [82(R)] |
| $(CH_3)_2CHCHO$ | 1a [1b] | 64 [62[d]] | 69(S) [72(R)] |
| $(CH_3)_3CCHO$ | 1a [1b] | 40 [40[d]] | 62(S) [60(R)] |

[c]Determined by chiral GLC.
[d]Yield of isolated product.

EXAMPLE 5

Synthesis of Vanadium(V) Salen Complexes

Solutions of (1R,2R)-N,N'-bis(3,5-di-tert-butylsalicyliden)-1,2-cyclohexanediamine (1.0 g, 1.8 mmol) in THF (20 mL) and vanadyl sulphate hydrate (0.55 g, 2.0 mmol) in hot ethanol (32 ml) were mixed and stirred under reflux for 2 h in air, then the solvent was removed in vacuo. The residue was dissolved in dichloromethane and put atop a $SiO_2$ filled column. Elution first with dichloromethane, then with EtOAc: methanol (2:1) gave a catalyst of formula 3b wherein $R^1=R^2$=tBu, $R^3\&R^4$=—$(CH_2)_4$— (0.6 g, 53%) as a dark-green crystalline solid. It can be additionally recrystallized from benzene-$CH_2Cl_2$. $[\alpha]_D^{23}$ −914.29 (c=0.01, $CHCl_3$); $\nu_{max}$ (KBr, cm⁻¹): 1618 ($\nu_{CH=N}$); 1250 ($\nu_{HSO4}$); 965 ($\nu_{V=O}$); $\delta_H$ ($CDCl_3$): 0.83 (3H, t), 1.33 (18H, s), 1.49 (18H, s), 1.7–2.2 (8H, m), 3.41 (2H, q), 3.81 (1H, m), 4.26 (1H, m), 7.49 (1H, s), 7.52 (1H, s), 7.68 (1H, s), 7.73 (1H, s), 8.53 (1H, s), 8.73 (1H, s).

EXAMPLE 6

Synthesis of Vanadium(V) Salen Complexes

By the method of Example 5, (1S,2S)-N,N'-bis(3,5-di-tert-butylsalicyliden)-1,2-cyclohexanediamine gave a catalyst of formula 3a wherein $R^1=R^2=tBu$, $R^3$ & $R^4=$—$(CH_2)_4$—.

EXAMPLE 7

Cyanation of Benzaldehyde Promoted by Vandium (V)-Catalyst

To a stirred mixture of KCN (12.37 g, 190 mmol), t-BuOH (3.7 g, 4.8 mL, 50 mmol), and benzaldehyde (5.21 g, 5 mL, 47.5 mmol) in dichloromethane (50 mL), $H_2O$ (0.5 mL, 31 mmol) was added. The reaction mixture was then cooled to −42° C. ($CH_3CN/CO_2$) and the catalyst (0.35 g, 0.475 mmol of the catalyst prepared in Example 2) in dichloromethane (20 mL) was added, followed by acetic anhydride (11.41 g, 10.55 mL, 190 mmol) in one portion. The reaction mixture was vigorously stirred for 10 hours at the same temperature. Solid salts were then filtered and washed thoroughly with dichloromethane. To remove the catalyst the reaction mixture was filtered through a pad of silica (10 mm×50 mm) eluting with dichloromethane. The solvent was evaporated in vacuo, and the resulting light green residue fractionated in vacuo giving the benzaldehyde cyanohydrin acetate. B.p. 95–97° C. (0.2 mm); yield 7.5 g (87.2%); ee (S), 90.3%.

What is claimed is:

1. A process for cyanating an aldehyde which comprises reacting the aldehyde with:
   i) a cyanide source which does not comprise a Si—CN bond or a C—(C=O)—CN moiety; and
   ii) a substrate susceptible to nucleophilic attack not comprising a halogen leaving group;
   in the presence of a chiral catalyst.
2. A process according to claim 1, in which the cyanide source is an alkali metal cyanide, preferably potassium cyanide.
3. A process according to claim 1 or 2, in which the substrate susceptible to nucleophilic attack not comprising a halogen leaving group is a carboxylic anhydride or carbonic acid anhydride.
4. A process according to claim 1 or 2, wherein the chiral catalyst comprises a complex of vanadium or titanium.
5. A process according to claim 4, in which the catalyst used is of the general formula

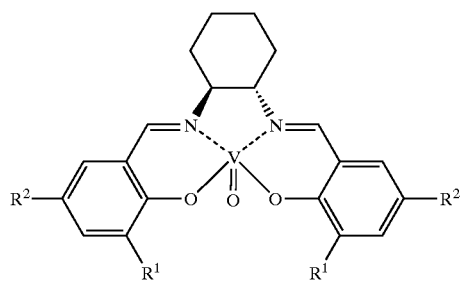

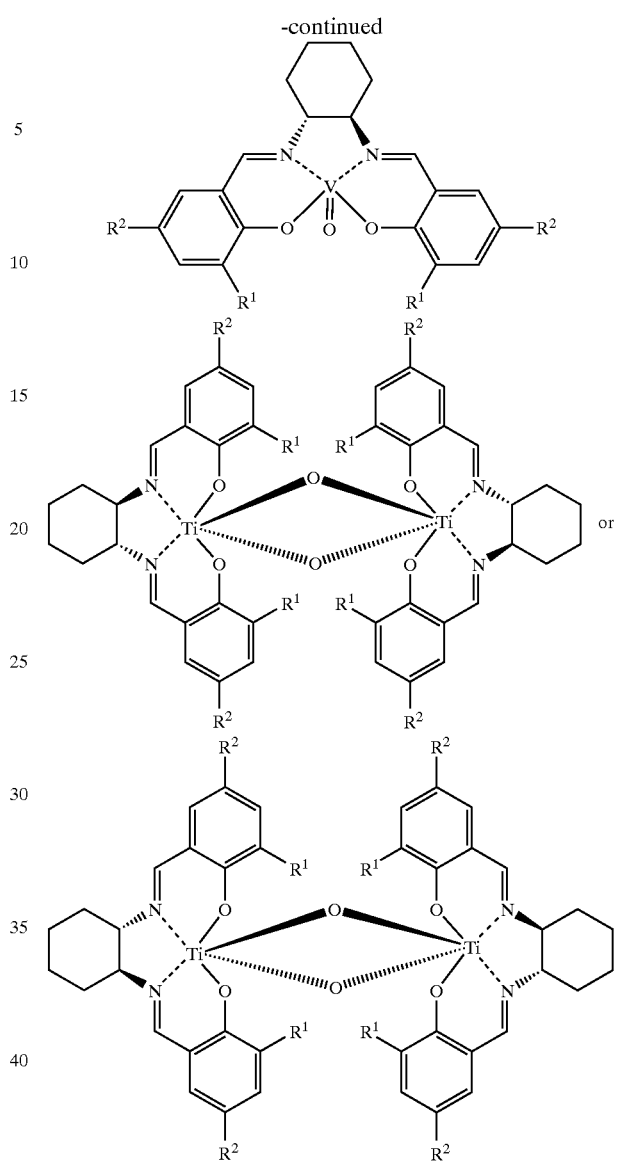

wherein each $R^1$ and $R^2$ are independently H, alkyl, aryl, aralkyl, alkoxy, aryloxy, halogen, nitro, halo-oalkyl, amino or amido.

6. A process according to claim 1 or 2, wherein the process is carried out in the presence of an additive having a pKa of greater than 10.
7. A process according to claim 6, wherein the additive is selected from pyridine, 2,6-lutidine, imidazole, t-butanol; and water.
8. A process according to claim 1 or 2, wherein the process is carried out in a polar, aprotic solvent.
9. A process according to claim 1 or 2, wherein the substrate susceptible to nucleophilic attack not comprising a halogen leaving group is added to a mixture of chiral catalyst, cyanide source, aldehyde, and optionally solvent and additive having a pKa of greater than 10.
10. A process for the cyanation of an aldehyde group which comprises reacting the aldehyde with:
    i) an alkali metal cyanide; and
    ii) a carboxylic anhydride;
    in the presence of a catalyst comprising a chiral complex of titanium or vanadium.

11. A process for the preparation of an O-acyl cyanohydrin which comprises reacting an aldehyde with potassium cyanide and a carboxylic anhydride in the presence of a catalyst comprising a chiral complex of titanium or vanadium.

12. A process according to claim 10 or 11, wherein the chiral complex of titanium or vanadium has the formula:

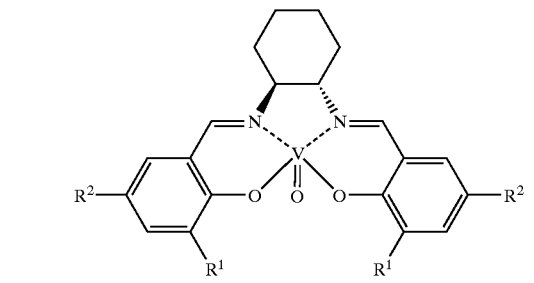

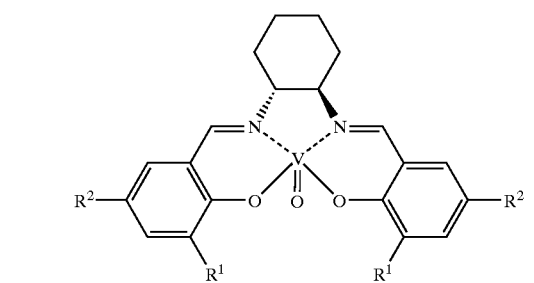

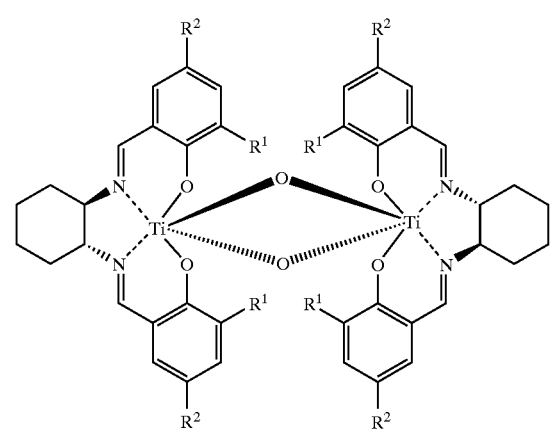

or

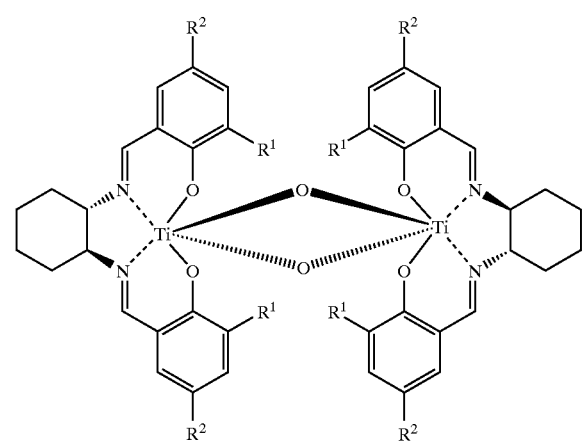

wherein each $R^1$ and $R^2$ are independently H, alkyl, aryl, aralkyl, alkoxy, aryloxy, halogen, nitro, halo-oalkyl, amino or amido.

13. A process as claimed in claim 1 wherein the chiral catalyst is a catalyst of formula (3a) or (3b):

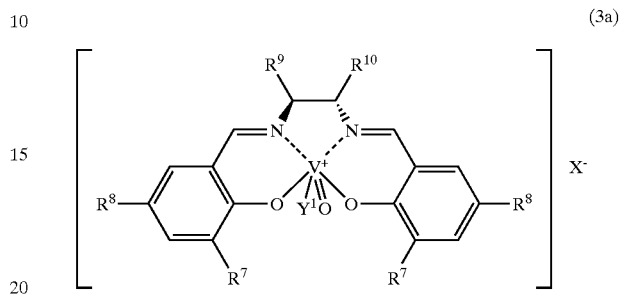

(3a)

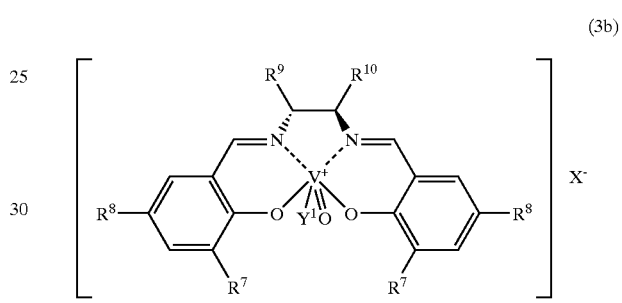

(3b)

wherein, $R^7$ and $R^8$ are independently hydrogren, halogen, cyano, nitro, hydroxy, amino, thiol, an optionally substituted hydrocarbyl, perhalogenated hydrocarbyl, an optionally substituted heterocyclyl, an optionally substituted hydrocarbyloxy, an optionally substituted mono or di-hydrocarbylamino, an optionally substituted hydrocarbylthio, an optionally substituted acyl, an optionally substituted ester, an optionally substituted carbonate, an optionally substituted amide, or an optionally substituted sulphonyl or sulphonamido group, or comprise part of a fused ring;

$R^9$ and $R^{10}$ are independently halogen, cyano, nitro, hydroxy, amino, thiol, an optionally substituted hydrocarbyl, perhalogenated hydrocarbyl, an optionally substituted heterocyclyl, an optionally substituted hydrocarbyloxy, an optionally substituted mono or di-hydrocarbylamino, an optionally substituted hydrocarbylthio, an optionally substituted acyl, an optionally substituted ester, an optionally substituted carbonate, an optionally substituted amide, or an optionally substituted sulphonyl or sulphonamido group, or $R^9$ & $R^{10}$ optionally are linked in such a way as to form an optionally substituted ring(s);

$Y^1$ is a neutral ligand; and

X is an anion.

14. A process as claimed in claim 10 wherein the catalyst is a catalyst of formula (3a) or (3b):

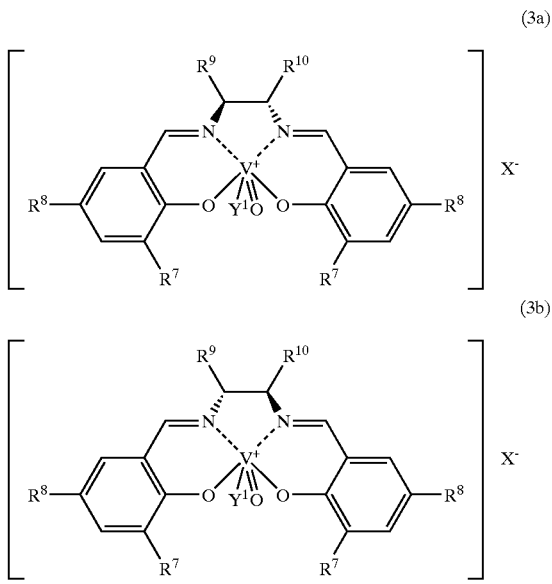
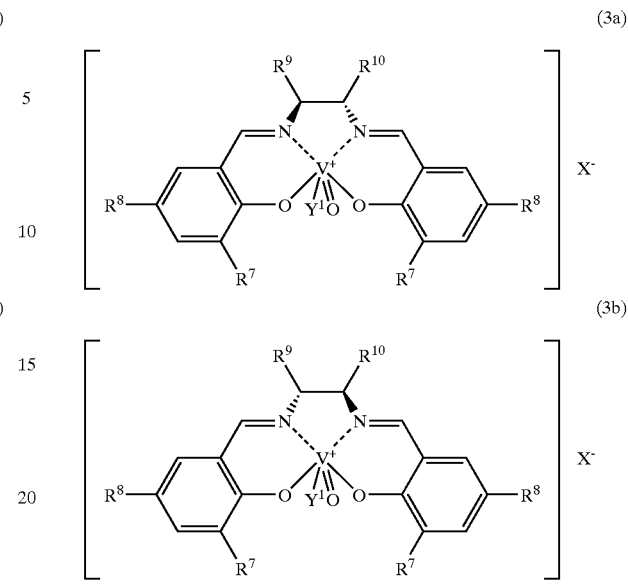

wherein,

R[7] and R[8] are independently hydrogen, halogen, cyano, nitro, hydroxy, amino, thiol, an optionally substituted hydrocarbyl, perhalogenated hydrocarbyl, an optionally substituted heterocyclyl, an optionally substituted hydrocarbyloxy, an optionally substituted mono or di-hydrocarbylamino, an optionally substituted hydrocarbylthio, an optionally substituted acyl, an optionally substituted ester, an optionally substituted carbonate, an optionally substituted amide, or an optionally substituted sulphonyl or sulphonamido group, or comprise part of a fused ring;

R[9] and R[10] are independently halogen, cyano, nitro, hydroxy, amino, thiol, an optionally substituted hydrocarbyl, perhalogenated hydrocarbyl, an optionally substituted heterocyclyl, an optionally substituted hydrocarbyloxy, an optionally substituted mono or di-hydrocarbylamino, an optionally substituted hydrocarbylthio, an optionally substituted acyl, an optionally substituted ester, an optionally substituted carbonate, an optionally substituted amide, or an optionally substituted sulphonyl or sulphonamido group, or R[9] & R[10] optionally are linked in such a way as to form an optionally substituted ring(s);

$Y^1$ is a neutral ligand; and

X is an anion.

15. A process as claimed in claim 11 wherein the catalyst is a catalyst of formula (3a) or (3b):

wherein,

R[7] and R[8] are independently hydrogen, halogen, cyano, nitro, hydroxy, amino, thiol, an optionally substituted hydrocarbyl, perhalogenated hydrocarbyl, an optionally substituted heterocyclyl, an optionally substituted hydrocarbyloxy, an optionally substituted mono or di-hydrocarbylamino, an optionally substituted hydrocarbylthio, an optionally substituted acyl, an optionally substituted ester, an optionally substituted carbonate, an optionally substituted amide, or an optionally substituted sulphonyl or sulphonamido group, or comprise part of a fused ring;

R[9] and R[10] are independently halogen, cyano, nitro, hydroxy, amino, thiol, an optionally substituted hydrocarbyl, perhalogenated hydrocarbyl, an optionally substituted heterocyclyl, an optionally substituted hydrocarbyloxy, an optionally substituted mono or di-hydrocarbylamino, an optionally substituted hydrocarbylthio, an optionally substituted acyl, an optionally substituted ester, an optionally substituted carbonate, an optionally substituted amide, or an optionally substituted sulphonyl or sulphonamido group, or R[9] & R[10] optionally are linked in such a way as to form an optionally substituted ring(s);

$Y^1$ is a neutral ligand; and

X is an anion.

* * * * *